US007491522B2

(12) United States Patent
Haraldsson et al.

(10) Patent No.: US 7,491,522 B2
(45) **Date of Patent: *Feb. 17, 2009**

(54) LIPASE-CATALYSED ESTERIFICATION OF MARINE OIL

(75) Inventors: Gudmundur G. Haraldsson, Reykjavik (IS); Arnar Halldorsson, Reykjavik (IS); Olav Thorstad, Porsgrunn (NO)

(73) Assignee: Pronova Biocare AS, Lysaker (NO)

( * ) Notice: Subject to any disclaimer, the term of this patent is extended or adjusted under 35 U.S.C. 154(b) by 75 days.

This patent is subject to a terminal disclaimer.

(21) Appl. No.: 10/534,708

(22) PCT Filed: Oct. 31, 2003

(86) PCT No.: PCT/NO03/00364

§ 371 (c)(1), (2), (4) Date: Oct. 13, 2005

(87) PCT Pub. No.: WO2004/043894

PCT Pub. Date: May 27, 2004

(65) Prior Publication Data

US 2006/0148047 A1 Jul. 6, 2006

(30) Foreign Application Priority Data

Nov. 14, 2002 (NO) .................................. 20025456

(51) Int. Cl.

*C12P 7/64* (2006.01)
*C12P 1/00* (2006.01)
*C12N 11/00* (2006.01)

(52) U.S. Cl. ......................... 435/134; 435/41; 435/135; 435/174; 435/176

(58) Field of Classification Search ................. 435/134, 435/41, 135, 174, 176

See application file for complete search history.

(56) References Cited

U.S. PATENT DOCUMENTS 6,518,049 B1 * 2/2003 Haraldsson et al. ......... 435/134

FOREIGN PATENT DOCUMENTS

GB 2350610 A * 6/2000
WO WO 95/24459 9/1995
WO WO 00/73254 A1 12/2000

OTHER PUBLICATIONS

Separation of Eicosapentaenoic Acid and Docosahexaenoic Acid in Fish Oil by Kinetic Resolution Using Lipase Gudmundur G. Haraldsson and Bjorn Kristinsson Journal of the American Oil Chemists Society vol. 75, No. 11 (1998).*

The preparation of concentrates of Eicosapentaenoic Acid and Docosahexaenoic acid by Lipase-catalyzed transesterification of fish oil with ethanol Gudmundur G. Haraldsson, Bjorn Kristinsson, Ragnheidur Sigurdardottir, Gudmundur G Gudmundsson, and Harald Breivik Journal of American Oil Chemists Society, vol. 74, No. 11 (1997).*

Haraldsson, G.G. et al. Separaton of Eicosapentaenoic Acid and-Docosahexaneoic Acid in Fish Oil by Kinetic Resolution Using Lipase, 1998, The Journal of American Oil Cchemists' Society, vol. 75, No. 11, pp. 1551-1556.*

Brevik, H. et al., Preparation of Highly Purified concentrates of Eicosapentaenoic Acid and Docosahexaenoic Acid, 1997, The Journal of American Oil Chemists' Society, vol. 74, No. 11, pp. 1462-1428.*

Gudmundur G. Haraldsson et al., "Separation of Eicosapentaenoic Acid and Docosahexaenoic Acid in Fish Oil by Kinetic Resolution Using Lipase," vol. 75, No. 11 (1998), pp. 1551-1556.

Gudmundur G. Haraldsson et al., "The Preparation of Concentrates of Eicosapentaenoic Acid and Docosahexaenoic Acid by Lipase-Catalyzed Transesterfication of Fish Oil with Ehtanol," vol. 74, No. 11 (1997), pp. 1419-1424.

Olivier Bousquet et al., "Counter-Current Chromatographic Separation of Polyunsaturated Fatty Acids," pp. 211-216.

Harald Breivik et al., "Preparation of Highly Purified Concentrates of Eicosapentaenoic Acid and Docosahexaenoic Acid," vol. 74, No. 11 (1997), pp. 1425-1429.

Database WPI, Week 199432, Derwent Publications Ltd., London, GB; AN 1994-260804 & JP 61 92683 A(Shokuhin Sangyo High Separation System), Jul. 12, 1994.

STN International, File CAPLUS, CAPLUS accession No. 1992:406541, Document No. 117:6541, Tanaka, Yukihisa et al: "Preparative separation of acylglycerol by centrifugal partition chromatography (CPC). II. Concentration of EPA (eicosapentaenoic acid) and DHA (docosahexaenoic acid) from lipase-hydrolized fish oil"; & Yukagaku (1992), 41(4), 312-16.

* cited by examiner

*Primary Examiner*—Daniel M Sullivan
*Assistant Examiner*—Yate' K Cutliff
(74) *Attorney, Agent, or Firm*—Fitzpatrick, Cella, Harper & Scinto

(57) ABSTRACT

Marine oil compositions which contain EPA and DHA as free acids or hexyl esters are esterified with ethanol in the presence of a lipase catalyst under essentially organic solvent-free conditions and separated by distillation.

22 Claims, No Drawings

LIPASE-CATALYSED ESTERIFICATION OF MARINE OIL

This invention relates to the lipase catalysed esterification of marine oils.

It is well known in the art to refine oil products of various kinds, including marine oils, with the aid of lipase catalysts whose specificity under the refining conditions employed enhances the recovery of a desired product.

Extensive research has been carried out in order to develop lipase-catalysed processes for isolating such commercially important PUFAs as EPA (eicosapentaenoic acid, C20:5) and DHA (docosahexaenoic acid, C22:6) from compositions such as fish oils containing them in relatively low concentrations.

For example, in PCT/NO95/00050 (WO 95/24459) we disclosed a process for treating an oil composition containing saturated and unsaturated fatty acids in the form of triglycerides to transesterification reaction conditions with a $C_{1-6}$ alcohol such as ethanol under substantially anhydrous conditions in the presence of a lipase active to preferentially catalyse the transesterification of the saturated and monounsaturated fatty acids. With the preferred lipases, *Pseudomonas* sp. lipase (PSL) and *Pseudomonas fluorescens* lipase (PFL) it was possible to prepare from marine oil sources concentrates containing more than 70% by weight of the commercially and therapeutically important omega-3 polyunsaturated fatty acids EPA and DHA in the form of glycerides.

A number of lipase-catalysed refining processes have utilised glycerol.

By way of example, JP 62-91188 (1987); WO91/16443; Int. J. Food Sci. Technol. (1992), 27, 73-76, Lie and Molin; Myrnes et al in JAOCS, Vol. 72, No. 11 (1995), 1339-1344; Moore et al in JAOCS, Vol. 73, No. 11 (1996), 1409-1414; McNeill et al in JAOCS, Vol. 73, No. 11 (1996), 1403-1407; WO96/3758 and WO96/37587 can be mentioned.

In PCT/NO00/00056 (WO 00/49117) we provided a process for esterifying a marine oil composition containing EPA and DHA as free fatty acids to form a free fatty acid fraction enriched in at least one of these fatty acids as compared to the starting composition, comprising the step of reacting said marine oil composition with glycerol in the presence of a lipase catalyst, *Rhizomucor miehei* lipase (MML), under reduced pressure and essentially organic solvent-free conditions, and recovering a free fatty acid fraction enriched in at least one of EPA and DHA. Preferably short-path distillation was used to separate the residual free fatty acids from the glyceride mixture.

However, it has now become evident that this strategy based on short-path distillation to separate the residual free fatty acids from the glyceride mixture is not very feasible. This is a result of too high volatility of the shorter chain monoglycerides, which contaminate the distillate to a large extent.

We have now discovered that lipase-catalysed processes for preparing concentrates of EPA and DHA by the direct esterification of free fatty acids with methanol or ethanol, or transesterification of $C_n$ alkyl esters from fish oil (n=2-18) with $C_m$ alcohol (alcoholysis) (m=1-12; n>m), and subsequent short-path distillation provide high DHA concentrates. These processes are fast and simple reactions offering excellent separation between EPA and DHA without generating unfavourable monoglycerides in the distillate. The essential features of the processes are defined in the attached patent claims.

In a preferred embodiment of the invention the $C_1$-$C_{12}$ alcohol is ethanol (ethanolysis). Among the $C_2$-$C_{18}$ alkyl esters, hexyl ester is preferred.

The molar ratio of methanol or ethanol to free fatty acids in the starting material in the direct esterification is from 0.5 to 10.0, the preferred ratio is from 0.5 to 3.0, and the most preferred ratio is from 1.0 to 2.0 or even from 1.0 to 1.5.

The molar ratio of $C_m$ alcohols to $C_n$ alkyl esters in the transesterification is from 0.5 to 10.0, the preferred ratio is from 0.5 to 3.0, and the most preferred ratio is from 2.0 to 3.0.

The esterifications are conducted at a temperature of 0° C. to 70° C., and preferably at a temperature of 20° C. to 40° C.

The lipase catalysts used in the present invention are immobilized on a carrier.

Some lipases used during the alcoholyses do have the properties that they catalyse the alcoholysis of DHA at a much slower speed than the corresponding alcoholysis of EPA. A preferred lipase having such properties is *Rhizomucor miehei* (MML). Other lipases have the property that they catalyse the alcoholysis of both EPA and DHA at a much slower speed than the corresponding alcoholysis of shorter chain and more saturated fatty acids. Lipases having such properties are *Pseudomonas* sp. lipase (PSL) and *Psedomonas fluorescens* lipase (PFL).

Direct esterification of fish oil free fatty acids with ethanol by MML is already known from G. G. Haraldsson and B. Kristinsson, J. Am. Oil Chem. Soc. 75: 1551-1556(1998).

Scheme 1.

Direct esterification of fish oil free fatty acids with ethanol by MML.

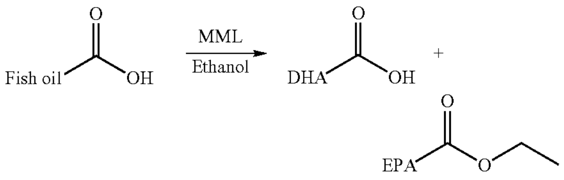

However, it was not believed that a satisfactory separation of the DHA residual free fatty acids and ethyl esters was possible by short-path distillation technique. Now we have surprisingly found that the short-path distillation technique can be used highly successfully. This is evident from the results shown in the examples below.

The present invention furthermore discloses ethanolysis of fish oil hexyl esters by a lipase, and subsequent molecular distillation to separate residual hexyl esters and more volatile ethyl esters.

Scheme 2.

Ethanolysis of fish oil hexyl esters by lipase (MML).

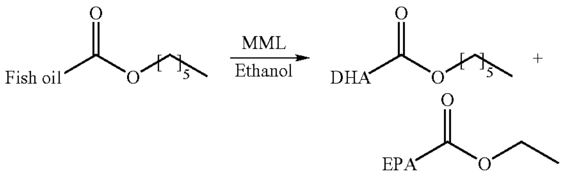

To further improve the recoveries of DHA and the concentration in the product an ethanolysis reaction as described in PCT/NO95/00050 (WO 95/24459) can be used as a pre-step before the direct esterification.

Scheme 3.
Ethanolysis of fish oil by lipase (MML).

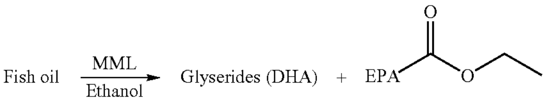

Prior to the direct esterification the glyceride mixture needs to be hydrolysed. In order to reduce the bulk of the starting material by half before hydrolysis the ethanolysis reaction of PCT/NO95/00050 (WO 95/24459) is found to be useful. The present invention therefore also discloses, as an alternative process, a two-enzymatic-step reaction starting with an ethanolysis and a subsequent direct esterification, each step followed by concentration by molecular distillation. This two-step reaction is also suitable for oils highly enriched with long-chain monounsaturates, such as Herring oil.

The two-step reaction is also applicable and advantageous when fish oil hexyl esters are the starting material.

The invention is illustrated by the Examples which follow.

Starting materials like Sardine oil (SO), Anchovy oil (AO), Herring oil (HO), Cod liver oil (CLO), Tuna oil (TO) and Blue whiting oil (BWO) have been tested.

Experimental Procedures

The bacterial lipases from *Pseudomonas* sp. (PSL; Lipase AK) and *Pseudomonas fluorescens* (PFL; Lipase PS) were purchased from Amano Enzyme Inc. The immobilized *Rhizomucor miehei* (MML; Lipozyme RM IM), *Thermomyces lanuginosa* (TLL; Lipozyme TM IM) and *Candida antarctica* (CAL; Novozym 435) lipases where provided by Novozyme in Denmark. The Sardine oil (14% EPA and 15% DHA), Anchovy oil (18% EPA and 12% DHA), Herring oil (6% EPA and 8% DHA), Tuna oil (6% EPA and 23% DHA), Cod liver oil (9% EPA and 9% DHA) and Blue whiting oil (11% EPA and 7% DHA) were all provided by Pronova Biocare.

Fatty acid analysis was performed employing a Perkin-Elmer 8140 Gas Chromatograph (GC) equipped with a flame ionisation detector (FID). Capillary column was 30 meter DB-225 30 N, 0.25 μm capillary column from J&W Scientific. The short-path distillation was carried out in a Leybold KDL 4 still. Nuclear magnetic resonance (NMR) spectra were recorded on a Bruker AC 250 NMR spectrometer in deuterated chloroform as solvent. Preparative thin-layer chromatography (TLC) was conducted on silica gel plates from Merck (Art 5721). Elution was performed with 80:20:1 mixture of petroleum ether: diethyl ether: acetic acid. Rhodamin G (Merck) was used to visualise the bands which subsequently were scraped off and methylated. Methyl ester of $C_{19:0}$ (Sigma) were added to the samples as internal standards before injection to GC.

Hydrolysis of Fish Oil

Fish oil (500 g, 0.55 mol) was added to a solution of sodium hydroxide (190 g, 4.75 mol), water (500 ml) and 96% ethanol (1.7 L). The resulting mixture was allowed to reflux for 30 minutes (until clear coloured liquid is observed) and then cooled to room temperature, stirring constantly. To neutralise the solution, 6.0 M hydrochloric acid (870 ml, 10% excess) was carefully added and the resulting mixture transferred to a separatory funnel. The free fatty acids were extracted twice with a 1:1 mixture of petroleum ether and diethyl ether (1.5 L). The organic layer was then washed three times with water (1.5 L) and dried over anhydrous magnesium sulphate. The drying agent was filtered off and the solvents removed by evaporation, finishing with high vacuum vaporisation for 2 hours at 50° C. Analysis on analytical TLC, a single spot indicated pure free fatty acids. The colour of the product varied from a yellowish to dark burgundy colour, depending on the fish oil.

Direct Esterification of Fish Oil Free Fatty Acids with Ethanol

Immobilized MML (15 g) was added to a solution of fish oil free fatty acids (300 g, approx. 1.03 mol) and absolute ethanol (143 g, 3.10 mol). The resulting enzyme suspension was gently stirred under nitrogen at 40° C. until desired conversion was reached. Samples were taken during the reaction and residual amount of free fatty acids detected by titration with 0,02M NaOH in order to monitor the progress of the reaction. Fractionation was performed by preparative TLC and each lipid fraction was subsequently quantified and analysed on fatty acid profile by GC. After reaching desired conversion the enzyme was removed by filtration and the excess ethanol evaporated in vacuo. The high DHA concentrate was obtained as residue after short-path distillation of the resulting mixture.

Ethanolysis of Fish Oil by Lipase

Immobilized MML (20 g) was added to a solution of fish oil (400 g, 0.44 mol) and absolute ethanol (61 g, 1.32 mol). The resulting enzyme suspension was gently stirred under nitrogen at room temperature until desired conversion was reached. Then the enzyme was removed by filtration and the excess ethanol evaporated in vacuo prior to short-path distillation. The progress of the reaction was monitored by analytical TLC and $^1$H-NMR. Fractionation was performed by preparative TLC and each lipid fraction was subsequently quantified and analysed on fatty acid profile by GC.

Hexanolysis of Fish Oil by Lipase

Immobilized CAL (25 g) was added to a solution of fish oil (500 g, 0.55 mol) and 1-hexanol (338 g, 3.31 mol). The resulting enzyme suspension was gently stirred under nitrogen at 65° C. until the triacylglycerols had been completely converted to hexyl esters, according to analytical TLC and/or $^1$H-NMR. The enzyme was removed by filtration and the excess hexanol evaporated in vacuo.

Ethanolysis of Fish Oil Hexyl Esters by Lipase

Immobilized MML (15 g) was added to a solution of fish oil hexyl esters (300 g, 0.80 mol) and absolute ethanol (111 g, 2.41 mol). The resulting enzyme suspension was gently stirred under nitrogen at 40° C. until desired conversion was obtained, according to $^1$H-NMR. The enzyme was removed by filtration and the excess ethanol evaporated in vacuo. The high DHA concentrate was obtained as residue after short-path distillation of the resulting mixture. The fatty acid composition of each ester group was determined by single run on GC.

EXAMPLE 1

Direct Esterification of Fish Oil Free Fatty Acids with Ethanol

Sardine Oil (SO)

The progress of direct esterification reaction of SO free fatty acids, containing 14% EPA and 15% DHA (14/15), with 3 equivalents of ethanol in the presence of MML (5% as based on the weight of free fatty acids) at 40° C. is displayed in Table 1. Under these conditions the lipase displayed extremely high activity toward the SO free fatty acids. Over 70% conversion (% ethyl esters) was reached after only 2 hours. After 4 hour reaction the residual free fatty acids contained 49% DHA and 6% EPA in 73% and 10% recoveries, respectively. In terms of DHA concentration and recoveries the optimal conversion appears to be around 75% conversion. In Table 1 the weight percentage of ethyl esters produced during the progress of the reaction was used directly as a measure of the extent of conversion.

TABLE 1

The progress of the direct esterification reaction of SO fatty acids (14/15) and ethanol by MML at 40° C.

| | Conv. | FA Comp. (FFA) | | Recovery | |
|---|---|---|---|---|---|
| Time | (mol %) | DHA % | EPA % | DHA % | EPA % |
| 1 h | 60 | 32 | 20 | 84 | 56 |
| 2 h | 71 | 43 | 11 | 80 | 21 |
| 3 h | 74 | 46 | 7 | 78 | 13 |
| 4 h | 77 | 49 | 6 | 73 | 10 |
| 5 h | 78 | 49 | 5 | 69 | 8 |
| 7 h | 80 | 50 | 5 | 65 | 7 |

Excellent results were obtained for direct esterification of SO free fatty acids after separation by short-path distillation. SO free fatty acids were reacted with ethanol in the presence of MML for 4 hours at 40° C. to reach 78% conversion. The free fatty acids of the reaction mixture comprised 49% DHA and 6% EPA with 75% DHA recoveries. After distillation at 115° C. the residue comprised 69% DHA and 9% EPA in 65% and 10% recoveries, respectively (Table 2). The recoveries of DHA were improved by slightly reducing the distillation temperature (see Table 3). We were not able to separate all the ethyl esters from the residual free fatty acids by the distillation. Despite that, we managed to obtain high DHA concentrate of approximately 90% free fatty acids and 10% ethyl esters after short-path distillation at 115° C. The ethyl esters obtained in the residue are highly enriched with DHA like the free fatty acids. Furthermore, the more saturated and shorter-chain free fatty acids are distilled resulting in higher DHA concentration of the residue than for the free fatty acid fraction after the reaction.

TABLE 2

The results from the direct esterification reaction of SO free fatty acids (14/15) and ethanol by MML at 40° C. and separation by distillation at 115° C.

| | | Fatty Acid Comp. | | Recovery | |
|---|---|---|---|---|---|
| Sample | Wt % | DHA % | EPA % | DHA % | EPA % |
| Ethyl ester (EE) | 78 | 4 | 19 | 25 | 95 |
| Free fatty acid (FFA) | 22 | 49 | 6 | 75 | 5 |
| Distillate (D) 115° C. | 85 | 7 | 15 | 35 | 90 |
| Residue (R) 115° C. | 15 | 69 | 9 | 65 | 10 |

The results for SO were improved by lowering the conversion and the distillation temperature as displayed in Table 3. After 4 hour reaction 75% conversion was obtained. After distillation at 111° C. the residue contained 66% DHA in 88% recoveries with DHA/EPA ratio of 4.7. At slightly higher distillation temperature the residue comprised 74% DHA in 75% recovery with a DHA/EPA ratio nearly seven. It should be notified that the DHA recovery after the distillations is based on percent weight of DHA in the starting oil.

TABLE 3

The results from the direct esterification reaction of SO free fatty acids (14/15) and ethanol by MML at 40° C. and separation by distillation at 111 and 113° C.

| | | Fatty Acid Comp. | | Recovery | |
|---|---|---|---|---|---|
| Sample | Wt % | DHA % | EPA % | DHA % | EPA % |
| EE | 75 | 3 | 17 | 23 | 87 |
| FFA | 25 | 47 | 7 | 77 | 13 |
| D 111° C. | 79 | 3 | 13 | 12 | 76 |
| R 111° C. | 21 | 66 | 14 | 88 | 24 |
| D 113° C. | 84 | 5 | 15 | 25 | 89 |
| R 113° C. | 16 | 74 | 11 | 75 | 11 |

The ethanol content can be reduced to 1 equivalent resulting in increased reaction time (Table 4). Less lipase can also be introduced resulting in considerably lower reaction rate.

TABLE 4

The progress of the direct esterification reaction of SO fatty acids (14/15) and 1 equivalent of ethanol by MML at 40° C.

| | Conv. | FA Comp. (FFA) | | Recovery | |
|---|---|---|---|---|---|
| Time | (mol %) | DHA % | EPA % | DHA % | EPA % |
| 5 h | 71 | 35 | 12 | 80 | 28 |
| 6 h | 73 | 41 | 11 | 79 | 26 |
| 7 h | 74 | 44 | 10 | 78 | 24 |
| 11 h | 77 | 45 | 7 | 76 | 18 |

Anchovy Oil (AO)

The progress of the direct esterification reaction of AO free fatty acids comprising 18% EPA and 12% DHA (18/12) under identical conditions to the SO is displayed in Table 5. As can be noticed a DHA/EPA ratio of approximately 6:1 was obtained at 82% conversion after 24 hours with EPA comprising 8% and DHA 50%. The DHA recovery was just below 80%. Also after 11 hours, at 79% conversion a DHA/EPA ratio of 5:1 with DHA recoveries as high as 84%. Therefore, AO and SO are both highly potential starting materials for making concentrates high in DHA and also, to make concentrates high in EPA from the ethyl ester fraction if that is of interest.

TABLE 5

The progress of the direct esterification reaction of AO free fatty acids (18/12) and ethanol by MML at 40° C.

| | Conv. | FA Comp. (FFA) | | Recovery | |
|---|---|---|---|---|---|
| Time | (mol %) | DHA % | EPA % | DHA % | EPA % |
| 2 h | 56 | 27 | 29 | 100 | 67 |
| 5 h | 73 | 37 | 19 | 93 | 27 |
| 8 h | 76 | 45 | 13 | 90 | 16 |
| 11 h | 79 | 50 | 9 | 84 | 10 |
| 24 h | 82 | 50 | 8 | 78 | 8 |

The results for AO are good in terms of DHA concentration and DHA/EPA ratios as displayed in Table 6. Free fatty acids of AO (19/12) were reacted as before to reach 76% conversion in 11 hours. After distillation at 121° C. the residue comprised 61% DHA in only 64% recovery with the DHA/EPA ratio being 5.5. The distillate may possibly be used to make high EPA concentrates by a repeated distillation at lower temperature. As an example a concentrate of 45% EPA and 10% DHA is considered to be a desirable composition for a potential commercial product.

TABLE 6

The results from the direct esterification reaction of AO free fatty acids (19/12) and ethanol by MML at 40° C. and separation by distillation at 121° C.

| | | Fatty Acid Comp. | | Recovery | |
|---|---|---|---|---|---|
| Sample | Wt % | DHA % | EPA % | DHA % | EPA % |
| EE | 76 | 2 | 21 | 10 | 84 |
| FFA | 24 | 45 | 13 | 90 | 16 |
| D 121° C. | 87 | 5 | 20 | 36 | 93 |
| R 121° C. | 13 | 61 | 11 | 64 | 7 |

Herring Oil (HO)

Free fatty acids from herring oil comprising 6% EPA and 8% DHA (6/8) were similarly treated under the direct esterification conditions as described above. The progress of the reaction is displayed in Table 7. The residual free fatty acids after 12 hour reaction contained 37% DHA and 6% EPA with 90% and 18% recoveries, respectively.

TABLE 7

The progress of the direct esterification reaction of HO free fatty acids (6/8) and ethanol by MML at 40° C.

| | Conv. | FA Comp. (FFA) | | Recovery | |
|---|---|---|---|---|---|
| Time | (mol %) | DHA % | EPA % | DHA % | EPA % |
| 4 h | 62 | 20 | 12 | 97 | 71 |
| 6 h | 70 | 24 | 12 | 96 | 61 |
| 8 h | 74 | 26 | 11 | 96 | 52 |
| 12 h | 80 | 37 | 6 | 90 | 18 |
| 24 h | 82 | 37 | 7 | 84 | 10 |

Free fatty acids from different HO comprising 9% EPA and 9% DHA (9/9) were reacted for 12 hours, to reach 84% conversion, in same way as before. The free fatty acids of the reaction mixture comprised 39% DHA and 8% EPA with 76% DHA recovery. After distillation at 110° C. the residue contained 40% DHA and 7% EPA in 68% DHA recovery with a DHA/EPA ratio of almost 6:1 (Table 8). Low DHA concentration results from high contents of long-chain monounsaturated fatty acids of 20:1 (4%) and 22:1 (37%). This high content of long-chain monounsaturates in HO and Capelin oil renders them less feasible starting material for the process described. A simple urea inclusion of the residual oil may be used to remove most of these monounsaturated fatty acids resulting in a valuable concentrate of DHA. It should be added that HO with its low EPA content is more suitable for obtaining high DHA/EPA ratios than SO and AO.

TABLE 8

The results from the direct esterification reaction of HO free fatty acids (9/9) and ethanol by MML at 40° C. and separation by distillation at 110° C.

| | | Fatty Acid Comp. | | Recovery | |
|---|---|---|---|---|---|
| Sample | Wt % | DHA % | EPA % | DHA % | EPA % |
| EE | 84 | 2 | 8 | 34 | 76 |
| FFA | 16 | 31 | 13 | 66 | 24 |

TABLE 8-continued

The results from the direct esterification reaction of HO free fatty acids (9/9) and ethanol by MML at 40° C. and separation by distillation at 110° C.

| | | Fatty Acid Comp. | | Recovery | |
|---|---|---|---|---|---|
| Sample | Wt % | DHA % | EPA % | DHA % | EPA % |
| D 110° C. | 82 | 4 | 10 | 32 | 88 |
| R 110° C. | 18 | 40 | 7 | 68 | 12 |

Tuna Oil (TO)

The progress of the direct esterification reaction of TO free fatty acids comprising 6% EPA and 23% DHA (6/23) under conditions identical to SO described above is displayed in Table 9 below. After 8 hour reaction conversion of 68% was obtained with the residual free fatty acids comprising 74% DHA and 3% EPA with 83% DHA recovery and a DHA/EPA ratio of 25:1 (Table 9). Clearly, this type of initial EPA/DHA composition of the starting oil is ideal for concentrating DHA.

TABLE 9

The progress of the direct esterification reaction of TO free fatty acids (6/23) and ethanol by MML at 40° C.

| | Conv. | FA Comp. (FFA) | | Recovery | |
|---|---|---|---|---|---|
| Time | (mol %) | DHA % | EPA % | DHA % | EPA % |
| 1 h | 43 | 47 | 9 | 98 | 78 |
| 2 h | 52 | 69 | 9 | 97 | 65 |
| 3 h | 62 | 68 | 9 | 96 | 50 |
| 5 h | 65 | 70 | 6 | 92 | 47 |
| 8 h | 68 | 74 | 3 | 83 | 14 |
| 11 h | 70 | 77 | 2 | 78 | 11 |
| 24 h | 73 | 74 | 2 | 71 | 8 |

Cod Liver Oil (CLO)

The progress of the direct esterification reaction of CLO free fatty acids comprising 9% EPA and 9% DHA (9/9) under similar conditions as described above is displayed in Table 10. Around 79% conversion a DHA/EPA ratio of 5:1 was obtained for the residual free fatty acids with 50% DHA concentration and over 80% recovery. These results are even better than those for SO and AO considering potential DHA recoveries. But in terms of cost, SO and AO are favoured over CLO. It may be of interest to compare the results of CLO (9/9) to those of HO (9/9) in light of the fact that CLO contains far less long-chain monounsaturates (20:1 and 22:1).

TABLE 10

The progress of the direct esterification reaction of CLO free fatty acids (9/9) and ethanol by MML at 40° C.

| | Conv. | FA Comp. (FFA) | | Recovery | |
|---|---|---|---|---|---|
| Time | (mol %) | DHA % | EPA % | DHA % | EPA % |
| 2 h | 65 | 37 | 20 | 96 | 62 |
| 3 h | 71 | 42 | 17 | 94 | 43 |
| 5 h | 75 | 46 | 13 | 91 | 27 |
| 8 h | 79 | 48 | 10 | 86 | 17 |
| 11 h | 80 | 50 | 7 | 76 | 12 |
| 24 h | 82 | 53 | 5 | 76 | 8 |

Blue Whiting Oil (BWO)

The progress of the direct esterification reaction of BWO free fatty acids comprising 11% EPA and 7% DHA (11/7) under the conditions described above is displayed in Table 11. Around 73% conversion the residual free fatty acids comprised 24% DHA in 95% recoveries. EPA was not transferred to ethyl esters as rapidly as expected. Interestingly, and unlike HO, the long-chain monounsaturated free fatty acids were to a much higher extent converted to ethyl esters. Higher conversion is needed to obtain better separation of EPA and DHA. The reason for the low conversion for BWO is unclear, but several attempts have not resulted in a higher conversion.

TABLE 11

The progress of the direct esterification reaction of BWO free fatty acids (11/7) and ethanol by MML at 40° C.

| Time | Conv. (mol %) | FA Comp. (FFA) DHA % | FA Comp. (FFA) EPA % | Recovery DHA % | Recovery EPA % |
|---|---|---|---|---|---|
| 4 h | 70 | 22 | 23 | 95 | 51 |
| 7 h | 71 | 23 | 23 | 95 | 50 |
| 9 h | 72 | 23 | 23 | 95 | 49 |
| 24 h | 73 | 24 | 21 | 95 | 44 |

EXAMPLE 2

Combined Ethanolysis and Direct Esterification of Fish Oil

A two-step reaction, starting with an ethanolysis and a subsequent direct esterification, each step followed by molecular distillation, could be used to improve the recoveries of DHA and the concentration in the product. Prior to the direct esterification the glyceride mixture obtained from the ethanolysis needs to be hydrolysed. Therefore, the ethanolysis reaction can be used as a pre-step, reducing the bulk of the starting material by half before hydrolysis. Notice the high recoveries obtained in the ethanolysis at 40° C. after separation by distillation (Table 12). Better results were obtained at room temperature as discussed above and displayed in Tables 13 and 14. The residue from the room temperature reaction comprised 23% DHA and 25% EPA in 97% and 65% recoveries, respectively (Table 13). These results indicate that the DHA recoveries can be improved significantly by the two-step process. Also, there is a dramatic reduction in the bulkiness for the hydrolysis reaction. Finally, this approach may be suitable for oils highly enriched with long-chain monounsaturates, such as HO.

TABLE 12

The results from the combined ethanolysis and direct esterification of AO. Ethanolysis of AO (19/12) with ethanol by MML at 40° C. and separation by distillation at 125° C., followed by direct esterification of the resulting free fatty acids with ethanol by MML at 40° C. and separation by distillation at 115° C.

| Sample | Wt % | Fatty Acid Comp. DHA % | Fatty Acid Comp. EPA % | Recovery DHA % | Recovery EPA % |
|---|---|---|---|---|---|
| D 125° C. | 41 | 1 | 14 | 3 | 27 |
| R 125° C. | 59 | 18 | 24 | 97 | 73 |
| D 115° C. | 66 | 4 | 22 | 12 | 69 |
| R 115° C. | 34 | 54 | 22 | 88 | 31 |

TABLE 13

The results from the ethanolysis reaction of AO (18/12) and ethanol by MML at room temperature and separation by distillation at 125° C.

| Sample | Wt % | Fatty Acid Comp. DHA % | Fatty Acid Comp. EPA % | Recovery DHA % | Recovery EPA % |
|---|---|---|---|---|---|
| D 125° C. | 47 | 2 | 15 | 3 | 35 |
| R 125° C. | 53 | 23 | 25 | 97 | 65 |

TABLE 14

The results from the ethanolysis reaction of AO (18/12) and ethanol by MML at 40° C. and separation by distillation at 125° C.

| Sample | Wt % | Fatty Acid Comp. DHA % | Fatty Acid Comp. EPA % | Recovery DHA % | Recovery EPA % |
|---|---|---|---|---|---|
| D 125° C. | 41 | 1 | 14 | 3 | 27 |
| R 125° C. | 59 | 18 | 24 | 97 | 73 |

EXAMPLE 3

Ethanolysis of Fish Oil Hexyl Esters

Ethanolysis of hexyl esters (HE) from fish oil is an alternative to the previously described ethanolysis of fish oil triglycerides (Scheme 2). The results indicate that various lipases including the *Rhizomucor miehei* lipase (MML) and the *Pseudomonas* lipases (PSL and PFL) can be used as well as the recently commercialised *Thermomyces lanuginosa* lipase (TLL) from Novozyme. Also, it has been confirmed that molecular distillation is quite suitable to separate residual hexyl esters and the more volatile ethyl esters.

*Candida antarctica* lipase (CAL) was used to convert AO triglycerides into the corresponding hexyl esters in a treatment with hexanol. Treatment of the resulting hexyl esters with ethanol and PSL followed by molecular distillation of the reaction mixture may afford residual hexyl esters with approximately 80% of EPA and DHA in a single or in two enzymatic steps. By concentrating DHA in the hexyl esters not only can we separate the ethyl esters from the hexyl esters but also distil off the more saturated hexyl esters as well. It may be possible to convert the hexyl esters into ethyl esters either chemically or enzymatically using CAL. Alternatively, it is possible to treat the anchovy oil hexyl esters in ethanolysis using MML that may afford 70% DHA in a single enzymatic step as hexyl esters. They may be further concentrated by an additional MML treatment. From the bulk of the ethyl esters containing most of the EPA it may be possible to purify EPA up to the ≧95% levels.

An alternative two-step approach is based on the ethanolysis of sardine oil to produce a concentrate of 50% EPA+DHA (30/20) as a glyceride mixture after molecular distillation. Treatment of the residual glycerides with hexanol and CAL affords hexyl esters of identical composition. They may either be treated with ethanol and PSL to afford hexyl esters with approximately 80% of EPA and DHA, or ethanol and MML to separate DHA from EPA, followed by further concentration of both EPA and DHA.

This process may have advantage in that the bulk of fish oil is being treated with ethanol instead of hexanol, which is both easier, less bulky and more feasible from industrial point of view. It must also be borne in mind that very high to excellent recovery of both EPA and DHA can be expected by that method.

Anchovy Oil (AO)

Like for the ethanolysis of fish oil triglycerides the fatty acid selectivity and activity of MML can be greatly affected by temperature. Thus, MML can be used to concentrate both EPA and DHA at or below 20° C., but at 40° C. EPA is separated from DHA resulting in high DHA concentrates. Anchovy oil hexyl esters comprising 18% EPA and 12% DHA were reacted with 2 equivalents of ethanol in the presence of MML (10% weight of the hexyl esters) for 24 hours at 40° C. to reach 59% conversion. After removal of the lipase excess ethanol was evaporated and the ethyl ester/hexyl ester (EE/HE) mixture distilled at 135° C. at $3\times10^{-3}$ mbar. The residue (26% weight) comprised 43% DHA in only 65% recovery. The DHA/EPA ratio was only 2.2 (Table 15).

TABLE 15

The results from the ethanolysis of AO hexyl esters (18/12) and ethanol by MML at 40° C. and separation by molecular distillation at 135° C.

| | | FA Comp. (HE) | | Recovery | |
|---|---|---|---|---|---|
| Sample | Wt %[a] | DHA % | EPA % | DHA % | EPA % |
| EE | 59 | 6 | 18 | 30 | 62 |
| HE | 41 | 21 | 13 | 70 | 38 |
| R 135° C. | 26 | 43 | 20 | 65 | 28 |

[a]In Tables 15 and 16 the conversion of the lipase catalysed reactions is based on mol percentage, whereas the distillation results are based on weight.

Interesting results were obtained when the reaction temperature was lowered to 20° C. in a similar reaction of Anchovy oil hexyl esters (18/13). After distillation at 135° C. the residue comprised 45% DHA and 30% EPA with 85% and 55% recoveries, respectively (Table 16).

TABLE 16

The results from the ethanolysis of AO hexyl esters and ethanol by MML at 20° C. and separation by molecular distillation at 135° C.

| | | FA Comp. (HE) | | Recovery | |
|---|---|---|---|---|---|
| Sample | Wt % | DHA % | EPA % | DHA % | EPA % |
| EE | 50 | 1 | 9 | 4 | 26 |
| HE | 50 | 23 | 25 | 96 | 74 |
| R 135° C. | 32 | 45 | 30 | 87 | 53 |

The *Pseudomonas* lipases were tested on a small scale with good results, giving high EPA recovery but considerably lower DHA recovery, especially if the reaction exceeded 50% conversion. The results of the ethanolysis reaction of AO (18/12) with 2 equivalents of ethanol in the presence of PSL and PFL at room temperature is displayed in Table 16. For PFL, after only 44% conversion of sardine oil hexyl esters in 24 hours, the content of 28% EPA and 21% DHA was obtained while 57% conversion for PSL in 24 hours yielded in 33% EPA and 17% DHA

TABLE 17

The results from the ethanolysis reaction of AO hexyl esters (18/12) and ethanol by PFL and PSL at room temperature.

| | Conv. | FA Comp. (HE) | | Recovery | |
|---|---|---|---|---|---|
| Sample | (mol %) | DHA % | EPA % | DHA % | EPA % |
| PFL | 44 | 21 | 28 | 81 | 89 |
| PSL | 57 | 17 | 33 | 53 | 79 |

The new Novozyme lipase (TLL), immobilized on granular silica gel, was compared to MML. The new lipase was found to be sensitive to ethanol and the activity decreased rapidly with increased temperature. At 20° C. both lipases were active and in 24 hours 54% conversion was obtained for MML but only 43% for TLL. The residual hexyl esters of TO, comprising 6% EPA and 28% DHA (6/28), from the TLL reaction contained 8% EPA and 45% DHA. The MML reaction resulted in residual hexyl esters containing 7% EPA and 54% DHA (Table 18). These lipases are obviously similar in fatty acid selectivity but TLL is more sensitive toward ethanol concentration, which makes it inferior to MML.

TABLE 18

The results from the ethanolysis reaction of TO hexyl esters (6/28) and ethanol by MML and TLL at room temperature.

| | Conv. | FA Comp. (HE) | | Recovery | |
|---|---|---|---|---|---|
| Sample | (mol %) | DHA % | EPA % | DHA % | EPA % |
| MML | 54 | 54 | 7 | 89 | 54 |
| TLL | 42 | 45 | 8 | 93 | 77 |

The results from the ethanolysis of TO hexyl esters (6/28) and ethanol at 40° C. are displayed in Table 19. Interestingly, at 40° C. only 15% conversion was obtained for TLL and 47% conversion for MML. It is believed that at higher temperature the lipase becomes more sensitive for the polar ethanol and its detrimental effects. For MML, after 47% conversion in 24 hours, the hexyl esters comprised 9% EPA and 49% DHA while only 15% conversion for TLL in 24 hours yielded 33% EPA and 17% DHA.

TABLE 19

The results from the ethanolysis reaction of TO hexyl esters (6/28) and ethanol by MML and TLL at 40° C.

| | Conv. | FA Comp. (HE) | | Recovery | |
|---|---|---|---|---|---|
| Sample | (mol %) | DHA % | EPA % | DHA % | EPA % |
| MML | 47 | 49 | 9 | 93 | 79 |
| TLL | 15 | 30 | 7 | 97 | 95 |

By the present invention separation of EPA and DHA by solvent free direct esterification of fish oil free fatty acids or fish oil hexyl esters and ethanol in the presence of a lipase is successfully obtained. The problems with monoglycerides in the distillate are avoided by the processes according to the present invention.

The invention claimed is:

1. A process for separating ethyl or methyl ester fraction enriched in EPA (eicosapentaenoic acid, C20:5) and a free fatty acid fraction enriched in DHA (docosahexaenoic acid, C22:6) from a mixture of such compounds that has been obtained by direct esterification of fish oil free fatty acids with ethanol or methanol using lipase, said process comprising the step of subjecting said mixture to molecular distillation.

2. A process according to claim 1, wherein said mixture of said EPA and DHA compounds has been obtained by a lipase catalysed alcoholysis of fish oil triglycerides, a subsequent molecular distillation that yields a residual glyceride mixture, and hydrolysis of the residual glyceride mixture.

3. A process for treating a marine oil composition containing EPA and DHA as $C_n$ alkyl esters of fatty acids (n=2-18) to form (1): a $C_n$ alkyl ester fatty acid fraction (n=2-18) enriched in DHA as compared to the starting material and a $C_m$ alkyl ester fatty acid fraction (m=1-12; n>m) enriched in EPA as compared to the starting material, or (2): a $C_n$ alkyl ester fatty acid fraction (n=2-18) enriched in both DHA and EPA as compared to the starting material and a $C_m$ alkyl ester fatty acid fraction (m=1-12; n>m) lower in both DHA and EPA as compared to the starting material comprising the step of reacting said marine oil composition with a $C_m$ alcohol (m=1-12; n>m) in the presence of a lipase catalyst under essentially organic solvent-free conditions, and separating the fractions by molecular distillation.

4. A process according to claim 3, wherein the starting mixture of $C_2$-$C_{18}$ alkyl esters is obtained by a lipase catalysed alcoholysis of fish oil triglycerides, a subsequent molecular distillation that yields a residual glyceride mixture, and alcoholysis of the residual glyceride mixture with a $C_2$-$C_{18}$ alkyl alcohol.

5. A process according to claim 3, wherein the $C_2$-$C_{18}$ alkyl ester is hexyl ester.

6. A process according to claim 3, wherein the $C_1$-$C_{12}$ alcohol is ethanol.

7. A process according to claim 3, wherein said lipase catalyst is *Rhizomucor miehei* lipase (MML), *Thermomyces lanuginosa* lipase (TLL), *Psedomonas* sp. lipase (PSL) or *Psedomonas fluorescens* lipase (PFL).

8. A process according to claim 1, wherein the molar ratio of methanol or ethanol to free fatty acids that is used in the direct-esterification step is from 0.5 to 10.0.

9. A process according to claim 8, wherein the molar ratio is from 0.5 to 3.0.

10. A process according to claim 8, wherein the molar ratio is from 1.0 to 2.0.

11. A process according to claim 8, wherein the molar ratio is from 0.5 to 1.5.

12. A process according to claim 3, wherein the molar ratio of $C_1$-$C_2$ alcohol to $C_2$-$C_{18}$ alkyl ester that is used in the lipase-catalyzed reacting step is from 0.5 to 10.0.

13. A process according to claim 12, wherein the molar ratio of $C_1$-$C_{12}$ alcohol to $C_2$-$C_{18}$ alkyl ester is from 0.5 to 3.0.

14. A process according to claim 12, wherein the molar ratio of $C_1$-$C_{12}$ alcohol to $C_2$-$C_{18}$ alkyl ester is from 2.0 to 3.0.

15. A process according to claim 4, wherein the $C_2$-$C_{18}$ alkyl ester is hexyl ester.

16. A process according to any of claims 1-14 and 15, wherein the esterification reaction is conducted at a temperature of 0° C. to 70° C.

17. A process according to claim 16, wherein the esterification reaction is conducted at a temperature of 20° C. to 40° C.

18. A process according to any of claims 1-14, wherein said lipase catalyst is immobilized on a carrier.

19. A process according to claim 1, wherein said lipase is one that catalyses the alcoholysis of DHA at a much slower speed than it catalyzes the corresponding alcoholysis of EPA.

20. A process according to claim 19, wherein said lipase catalyst is *Rhizomucor miehei* lipase (MML) or *Thermomyces lanuginosa* lipase (TLL).

21. A process according to claim 16, wherein said lipase catalyst is immobilized on a carrier.

22. A process according to claim 17, wherein said lipase catalyst is immobilized on a carrier.

* * * * *